(12) United States Patent
Essler et al.

(10) Patent No.: US 8,192,753 B2
(45) Date of Patent: *Jun. 5, 2012

(54) PH-SENSITIVE CATIONIC LIPIDS, AND LIPOSOMES AND NANOCAPSULES CONTAINING THE SAME

(75) Inventors: Frank Essler, Halle (DE); Steffen Panzner, Halle (DE); Gerold Endert, Halle (DE)

(73) Assignee: Marina Biotech, Inc., Bothell, WA (US)

( * ) Notice: Subject to any disclaimer, the term of this patent is extended or adjusted under 35 U.S.C. 154(b) by 1316 days.

This patent is subject to a terminal disclaimer.

(21) Appl. No.: 10/505,107

(22) PCT Filed: Feb. 19, 2003

(86) PCT No.: PCT/EP03/01661
§ 371 (c)(1),
(2), (4) Date: Aug. 16, 2005

(87) PCT Pub. No.: WO03/070220
PCT Pub. Date: Aug. 28, 2003

(65) Prior Publication Data
US 2006/0002991 A1    Jan. 5, 2006

(30) Foreign Application Priority Data
Feb. 19, 2002 (DE) .................. 102 07 177

(51) Int. Cl.
*A61K 9/127* (2006.01)
(52) U.S. Cl. ........ 424/450; 544/157; 544/243; 544/244; 546/22
(58) Field of Classification Search .................. None
See application file for complete search history.

(56) References Cited

U.S. PATENT DOCUMENTS
5,965,434 A    10/1999 Gurevich et al.
2003/0031704 A1    2/2003 Huang et al.

FOREIGN PATENT DOCUMENTS
JP    11199488    7/1999
JP    11217328    8/1999
WO    WO 0030444    6/2000
WO    WO 0126629    4/2001

OTHER PUBLICATIONS

Multiple Sclerosis, http://lib.bioinfo.pl/meid:7420 (2008).*
Hacks Chemical Dictionary, Fourth Edition, Julius Grant, 1972, p. 203.*
Merriam-Webster-Online-Dictionary; http://www.merriam-webster.com/dictionary/residue.*
Collins, Expert Opinion Investig Drugs (2007), 16(11), p. 1743-1751.*
MS, http://www.everydayhealth.com/multiple-sclerosis/multiple-sclerosis-prevention.aspx, 2011.*
MS2, http://en.wikipedia.org/wiki/Treatment_of_multiple_sclerosis, 2011.*
Profft et al., caplus an 1964:492356.*
Merriam-Webster-Online-Dictionary; http://www, merriam-webster.com/dictionary/residue (2008).*
Patent Abstracts of Japan; vol. 1999, No. 12, Oct. 29, 1999.
Patent Abstracts of Japan; vol. 1999, No. 13, Nov. 30, 1999.

* cited by examiner

*Primary Examiner* — Sun Jae Loewe
(74) *Attorney, Agent, or Firm* — Mintz Levin Cohn Ferris Glovsky and Popeo, P.C.; Ivan R. Elrifi

(57) ABSTRACT

The invention suggests a pH-sensitive cationic lipid with a $pK_a$ value between 3.5 and 8, according to the general formula cation-spacer-Y-spacer-X-lipid, wherein Y and X represent linking groups. Furthermore, liposomes are described, which liposomes include said optionally cationic lipids.

20 Claims, No Drawings

PH-SENSITIVE CATIONIC LIPIDS, AND LIPOSOMES AND NANOCAPSULES CONTAINING THE SAME

RELATED APPLICATIONS

This application is a national stage application, filed under 35 U.S.C. §371, of International Application No. PCT/EP03/01661, filed Feb. 19, 2003, which claims the benefit of German Patent Application No. 102 07 177.2, filed Feb. 19, 2002, the contents of which are incorporated by reference in their entireties.

The invention relates to pH-sensitive, cationic lipids, i.e., polar compounds based on amphiphilic molecules, the hydrophilic head group of which being substituted with one or more organic cations with a pK value between 3.5 and 8; the invention also relates to liposomes and nanocapsules containing said compounds, and to the use of such liposomes.

The term "lipids" summarizes three classes of natural materials which can be isolated from biological membranes: phospholipids, sphingolipids, and cholesterol, including its derivatives. Industrially produced compounds with similar properties are e.g. diacylglycerols or N,N-dialkylamines.

These substances are of technical interest in the production of liposomes. Inter alia, such liposomes can be used as containers for active substances in pharmaceutical preparations. In such uses, efficient and stable packaging of the cargo and controllable release of the contents are desirable. Both of these requirements are not easy to combine: the more stable and compact the packaging, the more difficult the release of the entrapped active substance therefrom. For this reason, liposomes changing their properties in response to an external stimulus, e.g. concentration, temperature or pH value, have been developed. Various thermosensitive and pH-sensitive liposomes are known in the art. The pH-sensitive liposomes are of special interest, because this parameter undergoes changes even under physiological conditions, e.g. during endocytotic reception of a liposome in a cell, or during passage of the gastrointestinal tract.

The following abbreviations will be used hereinafter:

| | |
|---|---|
| CHEMS | Cholesterol hemisuccinate |
| PC | Phosphatidyl choline |
| PE | Phosphatidyl ethanolamine |
| PS | Phosphatidyl serine |

Well-known pH-sensitive liposomes particularly comprise CHEMS. CHEMS, in mixture with phosphatidyl ethanolamine, is used to produce pH-sensitive liposomes, among other things (Tachibana et al. (1998); BBRC 251, 538-544, U.S. Pat. No. 4,891,208). Such liposomes can enter cells by endocytosis and are capable of transporting cargo molecules into the interior of cells on this route, without doing damage to the integrity of the cellular membrane.

One substantial drawback of CHEMS is its anionic character. Liposomes produced using same have a negative overall charge and, disadvantageously, are taken up by cells with low efficiency. Despite the transfer mechanism described above, they are barely suitable for the transport of macromolecules into cells.

For this purpose, the art uses cationic liposomes having a preferably high and constant surface charge. The positive overall charge of such particles leads to electrostatic adherence to cells and subsequently to efficient transport into same. The use of these compounds and of liposomes produced using same remains restricted to in vitro or ex vivo applications, because such positively charged liposomes disadvantageously result in uncontrolled formation of aggregates with serum components.

The disadvantages of well-known lipids and structures formed from such lipids can be summarized as follows: As a rule, the amounts of proteins, DNA or RNA which can be entrapped by anionic liposomes are below average, being insufficient for a variety of uses. By using well-known cationic liposomes, it is possible to entrap a suitable quantity of proteins or nucleic acids or derivatives thereof, but these structures frequently have critical cytotoxicity. However, membranes having enclosed a high amount of phosphatidyl ethanolamine to increase their fusogenic properties exhibit low stability. Accordingly, the well-known liposomes involve the drawbacks of (a) being unstable, (b) conveying insufficient material in the interior thereof, or (c) having excessive cytotoxicity.

Attempts of improving such disadvantageous properties are frequently accompanied by increased cytotoxicity and incompatibility with serum or blood. Some of the well-known lipids and liposomes comprising same do not necessarily have to imply all of the above drawbacks. However, no structures are known wherein as many as possible, i.e., at least two, preferably three or more of the above-mentioned drawbacks are absent.

The object of the invention was therefore to provide new compounds which can be produced easily and at low cost, do not exhibit the above-mentioned drawbacks, and i) allow stable entrapping of active substances in liposomes;

ii) aid in the production of liposomes capable of conveying an entrapped active substance into the interior of cells;

iii) the presence of which aids to achieve the production of cationic liposomes which can be mixed with serum, with no formation of major aggregates;

iv) can be incorporated in high amounts in liposomal membranes; and v) have good biodegradability and sufficient biological stability.

The invention accomplishes the above technical object by providing a pH-sensitive, cationic lipid with a $pK_a$ value between 3.5 and 8, according to general formula (I):

$$\text{Cation-spacer2-Y-spacer1-amphiphilic substance} \qquad (I)$$

wherein (a) the cation is selected from the group comprising imidazole, morpholine, piperazine, purine, pyridine and/or pyrimidine or derivatives thereof, (b) spacer 1 and/or spacer 2 are lower alkyl residues with up to 8 C atoms with linear, branched or cyclic structure and 0, 1 or 2 ethylenically unsaturated bonds, (c) Y comprises a deletion; —(C=O)—O—; —(C=O)—NH—; —NH—(C=O)—O—; —O—; —NH—; —CH=N—; —O—(O=C)—; —S—; —(O=C)—; —NH—(O=C)—; —O—(O=C)—NH—, —N=CH— and/or —S—S—, (d) the amphiphilic substance comprises a structure according to general formula (II) or (III):

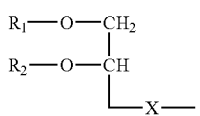

(II)

wherein
R₁ and R₂ independently are $C_8$-$C_{30}$ alkyl or acyl chains with 0, 1 or 2 ethylenically unsaturated bonds, and
X is selected from the group comprising a deletion, —O—(C=O); —NH—(C=O)—; —S—(C=O)—; —O—; —NH—; —S—; —N=CH—; —(O=C)—O—; —S—(O=C)—; —NH—(O=C)—; —N=CH— and/or —S—S—;

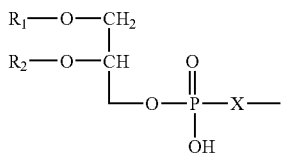

(III)

wherein
R₁ and R₂ independently are $C_8$-$C_{30}$ acyl chains with 0, 1 or 2 ethylenically unsaturated bonds, and
X is —O—.

Particular components will explained below:

Amphiphilic Substances

The amphiphilic substance comprises both membrane-forming and membranous compounds of a bilayer membrane. Preferred components of the compounds according to the invention are amphiphilic substances such as diacylglycerols, dialkylglycerols, phosphoglycerols, acylated or alkylated 3-amino-1,2-propanediols, because these compounds, in particular, are available at low cost, involve ordinary chemistry, and allow incorporation in membranes in high amounts without increasing the permeability thereof or even—completely—destroying their membrane character.

Also preferred are the amphiphilic substances diacylglycerols, dialkylglycerols, phosphoglycerols, acylated or alkylated 3-amino-1,2-propanediols. The long-chain alkyls or acyls present in these fragments comprise between 8 and 30 C atoms. They are preferably linear or slightly branched and may have 0, 1, or 2 ethylenically unsaturated bonds. Particularly preferred are substituents as found in natural lipids, i.e., straight-chain fatty acids or fatty alcohols having 12 to 20 C atoms, with zero, one or two unsaturated bonds. Still more preferred are lauroyl, myristoyl, palmitoyl, stearoyl, oleoyl, and linoleoyl residues or the corresponding fatty alcohols thereof. In general, the same applies to the long-chain alkyl residues of N,N-dialkylamines.

In a particularly preferred fashion dicarboxylic acids are used as polar head group of the amphiphilic substance, which, in particular, allow coupling of the actually charge-bearing substituents via additional functional groups. Preferred are the following amphiphilic substances derived therefrom: long-chain esters of 1,4- or 1,5-dicarboxylic acids, especially aspartic acid, glutamic acid, malic acid, tartaric acid, citric acid, aconitic acid, citraconic acid, maleic acid or similar compounds wherein the actually charge-bearing substituents are coupled via the remaining amino group, hydroxyl group, carboxylic group, or via the double bond.

Other advantageous amphiphilic substances are obtained from diamines with an additional functional group, e.g. in the form of a diamide of 3-aminoalanine, diaminobutyric acid, ornithine, or lysine with long-chain fatty acids.

Ultimately, the compounds according to the invention can also be produced in the form of derivatives of sphingosine or ceramide. They can also be prepared as derivatives of long-chain vinyl ethers or of plasmalogens.

The amphiphilic substances used with advantage as starting materials can be functionalized in their hydrophilic head group in various ways so as to conveniently allow easy and stable coupling or optionally to assume the function of a steric spacer. Particularly suitable for direct coupling are the hydroxyl group, the amino group, as well as carboxylic groups. Advantageously, the above coupling groups have good biodegradability.

Y and X represent linking functional groups, the presence of which is not compulsory in any event; it may also be envisaged that the value of Y and/or X is a deletion, i.e., these functional groups are absent. In a preferred fashion the linking group X comprises the structures —(C=O)—O—; —(C=O)—NH—; —NH—(C=O)—O—; —O—; —NH—; —CH=N— or —S—S—. Advantageously, the linking group Y corresponds in its structure to the group X, and may additionally comprise the structures —O—(O=C)—; —S—(O=C)—; —NH—(O=C)—; —O—(O=C)—NH—; or —N=CH—. For example, the Y group can be omitted in those cases where the cation can be coupled directly to the amphiphilic substance, e.g. in the esterification of imidazole-4,5-dicarboxylic acid with dipalmitoylglycerol.

Spacer:

Situated between the cation and amphiphilic substance are the molecular components spacer-Y-spacer-X. The spacer is a lower alkyl residue of linear, branched or cyclic structure, which has from 0 to 8 C atoms and includes 0, 1 or 2 ethylenically unsaturated bonds, preferably —CH₂—; —CH₂—CH₂— and/or —CH₂—CH₂—CH₂—. The spacer may have hydroxyl groups so as to increase the polarity of the molecule. In particular, the spacer can be a sugar. Advantageously, the spacer can also be a polyethylene glycol, and such a spacer may comprise up to 20 monomer units.

Cation:

The overall molecule assumes its pH-dependent charge characteristics by one or more organic cations with a $pK_a$ value between 3.5 and 8. Preferred molecules or molecular components with this property are nitrogen bases. These nitrogen bases are linked to the lipid via spacers and coupling groups, thus forming a compound according to the formula of the invention.

Coupling reactions result in amphiphilic organic cations, e.g. derived from the following classes of substances: o-, m-, p-anilines; 2-, 3- or 4-substituted anisidines, toluidines or phenetidines; 2-, 3-, 5-, 6-, 7- or 8-substituted benzimidazoles, 2-, 3-, 4- or 5-substituted imidazoles, 1- or 5-substituted isoquinolines, 2-, 3- or 4-substituted morpholines, 2-, 3- or 4-substituted picolines, 1-, 2- or 3-substituted piperazines, 2-, 5- or 6-modified pterines, 3-, 4-, 5-, 6- or 9-substituted purines, 2- or 3-substituted pyrazines, 3- or 4-substituted pyridazines, 2-, 3- or 4-modified pyridines, 2-, 4-, 5- or 6-substituted pyrimidines, 1-, 2-, 3-, 4-, 5-, 6- or 8-substituted quinolines, 2-, 4- or 5-substituted thiazoles, 2-, 4- or 6-substituted triazines, or derivatives of tyrosine. Particularly preferred are piperazines, imidazoles, morpholines, purines and/or pyrimidines.

In many cases, e.g. where the nitrogen bases are in the form of a ring system, positional isomers are existing, wherein the linking spacer is substituted to various positions of the organic cation. Such positional isomers fall within the disclosure of this invention. In many cases, the $pK_a$ values of the organic cation can be influenced via said positional isomerism alone. The relevant fundamental rules are well-known to those skilled in the art. Alternatively, these effects can be estimated from tabular compilations (Handbook of Chemistry and Physics, Vol. 73, pp. 8-37 ff.). In a preferred fashion $R_1$ and $R_2$ independently are $C_8$-$C_{30}$ alkyl or acyl chains with 0, 1 or 2 ethylenically unsaturated bonds, particularly lauroyl, myristoyl, palmitoyl, stearoyl, oleoyl, and linoleoyl residues or the corresponding alcohols thereof. Those skilled in the art are familiar with the option of using other amphiphilic substances, Y, X, $R_1$, $R_2$, spacers and/or cations in addition to the preferred amphiphilic substances, Y, X, $R_1$, $R_2$, spacers and/or cations; in this event, the preferred amphiphilic substances, Y, X, $R_1$, $R_2$, spacers and/or cations do not represent an essential component of the structures according to the invention. Furthermore, it can be advantageous to do without the spacer, Y and/or X.

In a preferred embodiment of the invention, the compound has a $pK_a$ value of between 3.5 and 7, preferably between 4 and 6.5. Advantageously, this $pK_a$ value falls in a range which is of crucial importance for the physiology of numerous organisms.

In another preferred embodiment of the invention the cations are derivatives of piperazines, imidazoles, morpholines, purines and/or pyrimidines.

Highly preferred are molecule fragments such as occurring in biological systems, particularly 4-imidazoles (histamines), 2-, 6- or 9-purines (adenines, guanines, adenosines, or guanosines), 1-, 2- or 4-pyrimidines (uracils, thymines, cytosines, uridines, thymidines, cytidines), or pyridine-3-carboxylic acids (nicotinic esters or amides).

Of course, the above-mentioned structural fragments may also have additional substituents. For example, these can be methyl, ethyl, propyl, or isopropyl residues, more preferably in hydroxylated form, including one or two hydroxyl groups. Also, these can be hydroxyl or keto functions in the ring system.

In addition, other structural fragments are also possible unless anionically dissociated molecule portions are formed in a pH range between 3.5 and 8.5, e.g. carboxylic acids, sulfonic acids, or some aromatic hydroxyl groups, or enols.

Nitrogen bases with preferred $pK_a$ values are also formed by single or multiple substitution of the nitrogen atom with lower alkanehydroxyls such as hydroxymethyl or hydroxyethyl groups. Suitable organic bases from this group are e.g. aminopropanediols, triethanolamines, tris(hydroxymethyl)-methylamines, bis(hydroxymethyl)methylamines, tris(hydroxyethyl)methylamines, bis(hydroxyethyl)methylamines, or the corresponding substituted ethylamines.

Nitrogen bases with preferred $pK_a$ values can also be found amongst aminosugars or aminosugar alcohols. Coupling of these fragments to the hydrophobic portion of the molecule may proceed either via the nitrogen of the base or via any of the hydroxyl functions.

In addition to derivatives including a single organic cation, those including two or three identical or different groups are also preferred. All of these groups are required to have a $pK_a$ value in the above-mentioned range. One suitable complex group is the amide of histamine and histidine or of histamine and histidylhistidine.

Anionic groups such as carboxylic acids, sulfonic acids, enols or aromatic hydroxyls are allowable as component of the molecule only if undissociated in the claimed pH range between 3.5 and 8.5. In general, this is the case if the $pK_a$ value is above 9.5.

In a preferred embodiment of the invention the amphiphilic substance is selected from

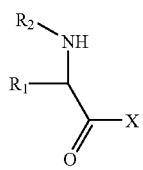

wherein
$R_1$ and $R_2$ independently are $C_8$-$C_{30}$ alkyl with 0, 1 or 2 ethylenically unsaturated bonds, and
X is selected from the group consisting of a deletion, —O—; —NH—; —S—.

Synthetic Methods:

Methods of performing chemical coupling of the individual molecule components are well-known to those skilled in the art and may vary depending on the starting material that is used and on the coupling component. Typical reactions are esterification, amidation, addition of amines to double bonds, etherification, or reductive amination.

Particularly preferred molecules can be prepared by
i) esterification of diacylglycerols,
ii) esterification or amidation of diacylglycerol hemi-succinate,
iii) addition of amines to the double bond of a diacylglycerol hemimaleate,
iv) amidation of phosphatidyl ethanolamine or phosphatidyl serine,
v) amidation or alkylation of 3-amino-1,2-propanediol diesters,
vi) oxidation of phosphatidyl glycerols and subsequent reductive amination, and
vii) reductive amination of glyceraldehyde and subsequent acylation.

Particularly preferred compounds which can be obtained by synthesis using the methods mentioned above include the following (Table 1), wherein $R_1$ represents the amphiphilic substance and ( )n represents additional molecule portions according to the spacer defined above.

TABLE 1

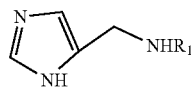

Histamine derivatives. An amphiphilic substance having a free carboxyl function is preferably coupled as an amide. Also preferred is amidation of phosphatidyl serine.

TABLE 1-continued

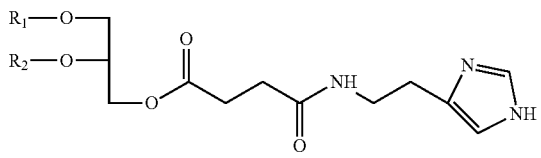 #59 Conjugation of histamine to dipalmitoylglycerol succinate. The $R_1$ and $R_2$ residues are acyl, alkyl or alkenyl groups.

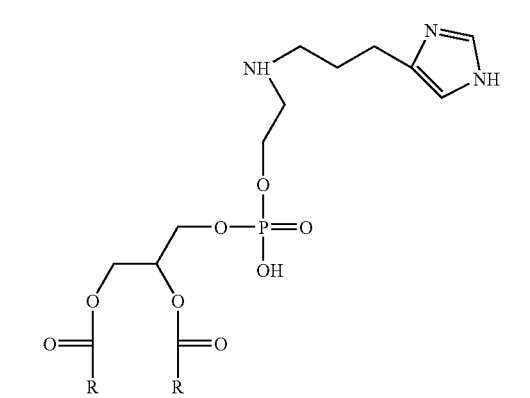 #30 Derivatives of phosphatidyl glycerol.
Advantageously, coupling is effected following oxidation of the terminal glycerol to form aldehyde and subsequent reductive coupling of the amphoteric substance. The example shows histamine. The R residues are alkyl or alkenyl groups.

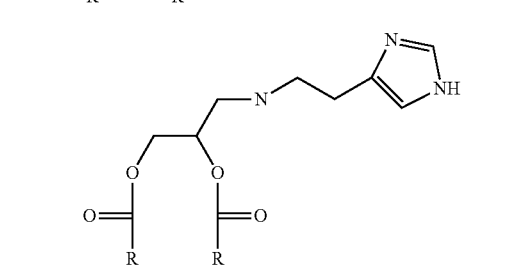 Conjugation of e.g histamine to glyceraldehyde and subsequent acylation. The R residues are alkyl or alkenyl groups.

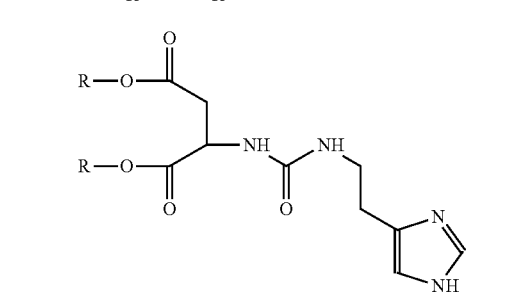 N-(Aspartyldihydroxyalkyl)-N'-histaminylurea.
The R residues are alkyl or alkenyl groups.

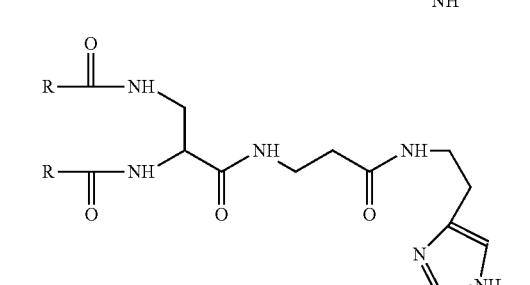 Diacylated dipeptide of 2,3-diaminopropionic acid, β-alanine and histamine.
The R residues are alkyl or alkenyl groups.

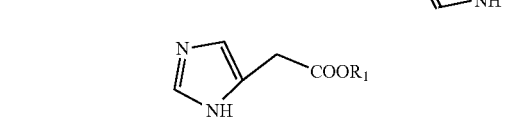 Derivatives of imidazoleacetic acid.
In a preferred fashion the amide can be formed using 3-amino-1,2-propanediols.

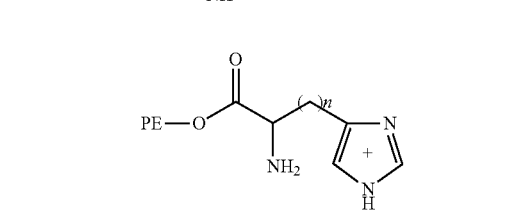 Histidine derivatives
The preferred compound shown on the left is formed by amide formation with phosphatidyl ethanolamine.

TABLE 1-continued

| | |
|---|---|
| 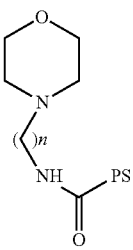 | Morpholine derivatives<br>The preferred compound shown on the left is formed by amide binding with the carboxyl of phosphatidyl serine. Other preferred derivatives can be formed e.g. with the carboxyl of diacylglycerol hemisuccinates. |
| 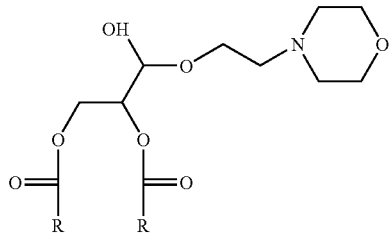 | Hemiacetal of an acylated glyceraldehyde and 2-hydroxy-morpholine. The R residues are alkyl or alkenyl groups. |
| 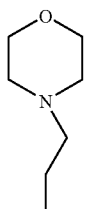 | Morpholinyiphosphatidyl ethanolamine<br>Obtainable e.g. by oxidation of 3-morpholino-1,2-propanediol and subsequent reductive amination with phosphatidyl ethanolamine. The R residues are alkyl or alkenyl groups. |
| 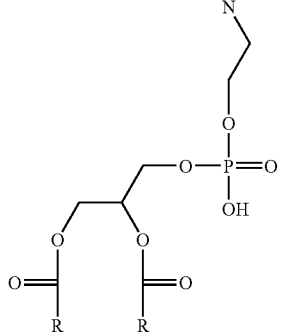 | #60 Conjugation of 4-(2-aminoethyl)morpholine to dipalmitoylglycerol succinate. The $R_1$ and $R_2$ residues are acyl, alkyl or alkenyl groups. |
| 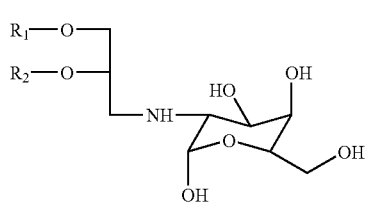 | Aminosugar derivative<br>Conjugation of e.g. glucosamine to glyceraldehyde and subsequent acylation. The R residues are acyl, alkyl or alkenyl groups. |
| 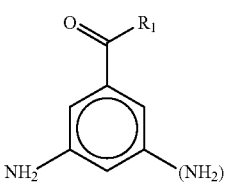 | Aminobenzoic acid or diaminobenzoic acid derivatives<br>Preferably, coupling of the amphiphilic substance is as an ester or amide of benzoic acid. The lipid can be a 3-amino-1,2-propanediol derivative, for example. |

The disclosure of the lipids according to the invention enables a person skilled in the art to provide equivalent compounds by means of routine tests, which compounds also fall within the scope of the teaching of the invention. A person skilled in the art will also recognize that the lipids according to the invention can be modified by addition, duplication, substitution, deletion, inversion or other procedures in order to adapt them to particular applications.

For example, addition may involve the process of adding the lipids with another cation, another spacer, another X, another Y and/or another amphiphilic substance. Obviously, addition of several other cations, spacers, Xs, Ys and/or amphiphilic substances to the lipid of the invention can also be envisaged. Furthermore, at least single duplication of particular regions of the lipid or of the overall lipid is possible. Similarly, a person skilled in the art will be familiar with the option of replacing particular components of the inventive lipids by components having a similar effect.

Furthermore, the structure of the lipids according to the invention can be modified in such a way that a particular sequence within the lipid or within a portion of the lipid will be modified so that e.g. the cation will be bound directly to the amphiphilic substance and spacers will be bound to the amphiphilic substance via X or Y, and, in the meaning of the invention, such compounds would involve functions substantially analogous to the lipids according to the invention. Furthermore, it is possible to remove an entire region from the lipid and re-incorporate it reversely. Those skilled in the art of chemistry will be familiar with the fact that virtually any option of modification and mutation existing e.g. in the field of peptide nucleic acid chemistry can also be applied in the field of lipid chemistry in an analogous manner.

The invention also relates to liposomes comprising the substances according to the invention. Advantageously, all of the substances or compounds of the invention can be incorporated in high amounts in liposomal membranes, resulting in a positive charge of the overall particle only if the pH value of the medium is smaller than ($pK_a+1$) of the compounds according to the invention.

In one particular embodiment of the invention, the amount of pH-sensitive cationic lipid is 50 mole-% at maximum, particularly 40 mole-%, and preferably 30 mole-%.

Compositions including at least 5 mole-% of compound, preferably 7 mole-%, more preferably 10 mole-%, especially preferably 15 mole-%, but 40 mole-% at maximum, are particularly preferred. Compositions including at least 10 mole-% of pH-sensitive cationic lipid and 30 mole-% at maximum are most preferred.

Another embodiment wherein the liposomes specifically comprise phosphatidyl choline, phosphatidyl ethanolamine and/or diacylglycerol is also convenient. Cholesterols themselves are incapable of forming liposomes, and therefore, addition of further lipid is necessary. In particular, this lipid can be a phospholipid. Obviously, further modifications of the liposome are possible. Thus, the use of polyethylene glycol-modified phospholipids or analogous products is particularly advantageous.

To produce amphoteric liposomes, anionic lipids such as phosphatidyl glycerol, phosphatidyl serine, phosphatidic acid, or CHEMS can be added, where the amount of anionic lipids must not exceed the amount of pH sensitive cationic lipids; instead, it must be smaller. Forming no aggregates with serum components, such amphoteric liposomes have improved compatibility in in vivo applications.

In another embodiment of the invention, the liposomes have an average size of between 50 and 1000 nm, particularly between 50 and 300 nm, and more preferably between 60 and 130 nm.

In another preferred embodiment, the liposomes comprise water-soluble active substances. In particular, the liposomes according to the invention are suitable for parenteral application. They can be used e.g. in cancer therapy and in the therapy of severe infections. To this end, liposome dispersions can be injected, infused or implanted. Thereafter, they are distributed in the blood or lymph or release their active substance in a controlled fashion as a depot. The latter can be achieved by highly concentrated dispersions in the form of gels. The liposomes can also be used for topical application on the skin. In particular, they may contribute to improved penetration of various active substances into the skin or even passage through the skin and into the body. Furthermore, the liposomes can also be used in gene transfer. Due to its size and charge, genetic material is usually incapable of entering cells without an aid. For this purpose, suitable carriers such as liposomes or lipid complexes are required which, together with the DNA, are to be taken up by the respective cells in an efficient and preferably well-directed fashion.

Advantageously, liposomes produced using the substances of the invention show low non-specific binding to cell surfaces. Specifically, this is the case when using additional anionic lipids in the production thereof. It is this low non-specific binding which is an essential precondition for achieving specific binding to target cells. Target control of the vehicles is obtained when providing the above-described liposomes with additional ligands. As a result, the active substance can be accumulated specifically in such cells or tissues which exhibit a pathological condition.

One important use of the substances according to the invention is therefore in the construction of vectors for the transfer of active substances in living organisms. The vectors are particularly suited for the transport of therapeutic macromolecules such as proteins or DNA which themselves are incapable of penetrating the cell membrane or undergo rapid degradation in the bloodstream.

In a preferred embodiment of the invention, the liposomes comprise a protein, a peptide, a carbohydrate structure, a DNA, an RNA, an antisense nucleotide, and/or a decoy nucleotide as active substance.

In a particularly preferred embodiment of the invention, at least 50 µg, preferably more than 80 µg, more preferably more than 100 µg, and especially preferably more than 140 µg of active substance per mg lipid is present inside the liposome.

The invention also relates to nanocapsules comprising the lipids and/or liposomes according to the invention. Various ways of providing liposomal nanocapsules are known to those skilled in the art. For example, WO 00/28972 and/or WO 01/64330 disclose various methods of generating nanocapsules, which hereby are incorporated in the disclosure of the present application.

The invention also relates to the lipids, liposomes and/or nanocapsules according to the invention for use as medical active substances. In a preferred fashion the therapeutically effective compounds are not restricted to specific indications. By virtue of the disclosure of the teaching according to the invention, the structures of the invention are provided for use in therapy, i.e., it advantageously encompasses any specific indication.

In a preferred embodiment of the invention the active substance is an active substance used in prophylaxis, diagnosis, therapy, course monitoring and/or aftercare especially of diseases. Of course, loading with a second active substance of the lipids, liposomes and/or nanocapsules used as active substances can be envisaged (used in a synonymous fashion hereinafter). If the active substance is an active substance used in prophylaxis, it can be a substances which e.g. is suitable in vaccination. In diagnosis, the lipids, liposomes and/or nanocapsules are used in vivo, in vitro or ex vivo to detect pathogenic modifications in an organism or in a tissue culture or in another isolated component of the body. When using the lipids, liposomes and/or nanocapsules in therapy, curing of diseases and restoration of the healthy initial condition or achieving the non-pathogenic initial condition is attempted, where absence of a particular disease does not imply that the organism could not exhibit other pathogenic changes. That is, when using the inventive structure in treatment and curing of a viral disease, the organism still may include a tumor disease which initially will not be co-treated therein. Obviously, simultaneous or time-shifted treatment of more than one disease with the structures of the invention can also be envisaged. For example, course monitoring can be a diagnosis performed at time intervals in parallel with a therapy. In this event, treatment of metabolic diseases, cancerous diseases, immunological diseases or genetic diseases can be concerned. The therapeutic success then is monitored and supervised by means of the lipids, liposomes or nanocapsules used in the course monitoring. Aftercare includes especially diagnostic and therapeutic operations following partial or substantial curative success.

The invention also relates to a pharmaceutical composition comprising at least one inventive lipid, at least one inventive liposome and/or one inventive nanocapsule, optionally together with a pharmaceutically tolerable carrier. In particular, use of the inventive structures, including an active substance or not, as pharmaceutical composition can be envisaged.

In particular, the pharmaceutical composition can be used as a drug. To this end, the lipids and/or liposomes and/or nanocapsules can be modified according to methods well-known to those skilled in the art. Advantageously, the liposomes according to the invention will not be attacked by complement components or perforin and thus can be used to transport active substances.

According to the invention, drugs or pharmaceutical compositions—used in a synonymous fashion herein—are substances and formulation of substances, particularly lipids, liposomes and/or nanocapsules, intended to cure, alleviate or avoid diseases, illness, physical defects or pathological affection by application on or in the human body. According to the invention, medical adjuvants or carriers are substances used as active ingredients in the production of drugs. Pharmaceutical-technical adjuvants serve to suitably formulate the drug or pharmaceutical composition and, if required during the production process only, can even be removed thereafter, or they can be part of the pharmaceutical composition as pharmaceutically tolerable carriers. Drug formulation or formulation of the pharmaceutical composition is optionally effected in combination with a pharmaceutically tolerable carrier and/or diluent. Examples of suitable pharmaceutically tolerable carriers include phosphate-buffered saline solutions, water, emulsions, gels, sterile solutions, etc. Drugs or pharmaceutical compositions comprising such carriers can be formulated by means of well-known conventional methods. These drugs or pharmaceutical compositions can be administered to an individual at a suitable dose, e.g. in a range of from 1 µg to 10 g of lipids, liposomes and/or nanocapsules per day and patient, with and/or without enclosed active substance. Doses of from 1 mg to 1 g are preferred, and this applies to the lipids, liposomes, nanocapsules and/or to the active substance transported by same. Administration of doses as few and as low as possible is preferred, and more preferably of a single or multiple dose. Administration can be effected on various routes, e.g. intravenous, intraperitoneal, intrarectal, intragastrointestinal, intranodal, intramuscular, local, e.g. intratumoral, but also subcutaneous, intradermal or as administration on the skin or via the mucosa.

Administration can also be effected in the form of a gene therapy, wherein the lipids, liposomes and/or nanocapsules are used to transport nucleic acids.

More specifically, the pharmaceutical compositions or the drugs comprise a pharmacological substance which is entrapped or bound by the lipids, liposomes and/or nanocapsules. Administration thereof can be effected either alone or together with appropriate adjuvants described in connection with drugs or pharmaceutical compositions, or in combination with one or more adjuvants, e.g. QS-21, GPI-0100 or emulsions such as Montanide adjuvants, DNA compounds such as CpG, Detox, bacterial vaccines, salts such as calcium phosphates and/or other suitable material enhancing the drug effect, preferably immunostimulatory molecules such as interleukins, e.g. IL-2, IL-12, IL-4 and/or growth factors such as GM-CSF. They are mixed with the inventive lipids, liposomes and/or nanocapsules according to well-known methods and administered in suitable formulations and doses. Formulation, dosages and suitable components are well-known to those skilled in the art.

Obviously, the pharmaceutical composition or the drug may also be a combination of two or more of the inventive pharmaceutical compositions or drugs, as well as a combination with other drugs, such as antibody therapies, chemotherapies or radiotherapies, administered or applied at the same time or separately in time in a suitable fashion. The production of the drugs or pharmaceutical compositions proceeds according to well-known methods.

The invention also relates to a kit comprising at least one inventive lipid, at least one inventive liposome, at least one inventive nanocapsule and/or an inventive pharmaceutical composition, optionally together with information how to combine the contents of the kit and/or for providing a formulation and an algorithm of administering said formulation, i.e., at which dose or time intervals particular components of the kit are administered to a patient, in particular. However, the recipient in the meaning of the invention may also be a cell or a tissue in vivo, ex vivo or in vitro. For example, the information can be an instruction leaflet or an information which the user can obtain via phone or internet. The algorithm of administering the formulation particularly includes instructions referring to the diagnostic and/or therapeutic procedure of treating a patient. The procedures can be single-step or multi-step procedures, as well as procedures carried out in the presence or absence of a physician. That is, the therapy regimen or the information thereon can be part of the kit.

The invention also relates to the use of the inventive lipids, the inventive liposomes, the inventive nanocapsules, the inventive kit and/or to the use in the production of a drug for the treatment of diseases, especially for the treatment of genetic, immunologic, metabolic diseases or cell growth disorders, preferably autoimmune diseases, blood flow diseases, tumor diseases, immunodeficiency diseases, diseases involving single organs or complete regions of organs or tissues, as well as diseases originally caused by viruses, bacteria or parasites.

The invention also relates to a method of loading liposomes with active substances, wherein one defined pH value is used for encapsulation, and a second pH value is adjusted to remove unbound active substance.

The invention also relates to the use of the liposomes in the production of nanocapsules.

The invention also relates to the use of the liposomes in the production of release systems in diagnostics.

Advantageously, the liposomes are used for the transport and/or release of active substances.

In another embodiment, the liposomes conveniently are used as depot formulation and/or as circulative depot.

In particular, the liposomes can be used with advantage in intravenous or peritoneal applications.

In another embodiment of the invention, the liposomes are used with advantage as vector to transfect cells in vivo, in vitro or ex vivo.

Surprisingly, it has also been found that amounts of proteins or DNA above average can be enclosed in liposomes including the compounds described herein in the membranes thereof. The efficiency of such incorporation depends on the pH value of the solution employed. Therefore, a process for efficient encapsulation of proteins or DNA in liposomes can be performed by initially adjusting a pH value that would result in good binding of the cargo molecules in the liposomes. With DNA as polyanion, low pH values of about 4 to 5 are used. With proteins, a useful pH value will depend on the isoelectric point of the protein, which should be below the $pK_a$ value of the substance according to the invention. Encapsulation is particularly effective when the pH value of the medium is selected so as to range between the isoelectric point of the protein and the $pK_a$ value of the optionally cationic lipid. The proteins then will have a negative charge, while the lipid layer already has a positive net charge.

If necessary, non-incorporated cargo molecules adhering on the outside can be removed by simply increasing the pH value. This step is necessary in all those cases where non-incorporated cargo molecules would give rise to aggregation of the liposomes. One advantageous fact when using the components of the invention is that the entrapped active substances must be maintained under conditions allowing interaction with the lipid layer only during the period of actual enclosure. Once the lipid layer remains closed in itself, it is possible to change to other conditions. Thereby, possible inactivation of active substances, particularly of proteins, can be minimized.

Liposomes comprising the components of the invention can be coated with polymers under conditions well-known to those skilled in the art, where single or multiple deposition of such substances on the surface is possible, in particular. In multiple deposition, optionally in the presence of crosslinkers, liposomal nanocapsules are formed as described in WO 00/28972 or WO 01/64330, which hereby are incorporated in the disclosure of the invention.

One advantageous fact when using the substances described herein is that the electrostatic interaction with the polyelectrolyte can be interrupted. As is well-known, the interaction of a polyelectrolyte with charge carriers of the liposomal membrane may give rise to demixing of membrane components and formation of lipid clusters. In many cases, such demixing is accompanied by a permeabilization of the liposomes. The substances of the invention allow elimination of this interaction following the coating process. When increasing the pH value at this point in time, the liposomes will be entrapped in the nanocapsules merely in a steric fashion, and interaction between the membrane and the polyelectrolytes does no longer exist. In this way, cluster formation of lipids and associated permeabilization of the membrane can be circumvented.

In one variant of the teaching according to the invention, these changes in permeability are used in a well-directed fashion in loading liposomes. To this end, an active substance to be enclosed can be added to a medium under conditions of high permeability, followed by adjusting conditions of low permeability. In this way, the active substance will remain inside the liposomes. Thereafter, non-entrapped active substance can be removed, if necessary. Such changes in permeability can be induced on liposomes or on liposomal nanocapsules.

Surprisingly, it has also been found that the liposomes according to the invention readily undergo fusion with other membranes at low pH values. In general, this step requires the presence of a larger amount of PE in the membrane. As a result of its tendency of forming hexagonal phases, said PE assumes the function of a helper lipid. However, the inferior stability of such membranes is disadvantageous, and gradual release of entrapped active substances is frequently observed.

However, liposomes produced using the substances according to the invention undergo effective fusion even in the absence of such a helper lipid. Thus, when using the substances of the invention, it is possible to produce liposomes which are capable of stably encapsulating an active substance, but undergo fusion with cell membranes under the conditions of low pH values to release the active substance there.

One essential precondition for the use of liposomes for experimental or therapeutic purposes is their compatibility with cells and tissues. A number of well-known compounds used to incorporate DNA or proteins in cells (for example, the cationic lipid DOTAP) are cytotoxic.

Surprisingly, it has been found that some of the compounds of the invention exhibit reduced cytotoxicity. In particular, this applies to those cases where the compounds include physiological components such as amino acids.

Another precondition for the construction of vectors to be used in gene or protein transport into cells is their compatibility with serum or blood. Due to their strong cationic charge, vectors known at present form uncontrollable large aggregates with serum, resulting in formation of thrombi in the organism. Their use in vivo is therefore practically impossible and is restricted to in vitro or ex vivo applications.

Surprisingly, it has been found that liposomes constructed using the components of the invention do not form any aggregates in serum or blood.

Another precondition for the construction of vectors to be used in protein or gene transfer is their stability under physiological conditions. Upon application into the blood circulation, liposomes are attacked by components of the complement system and undergo rapid lysis. This reaction proceeds within minutes. As a result, pores are formed in the membrane, which allow even large molecules such as proteins to diffuse out therethrough. At present, stabilization of liposomes with respect to this mechanism is only possible by incorporating cholesterol in the lipid layer. While such liposomes are highly stable, they are no longer able to interact with cells or readily release their active substance. Surprisingly, it has been found that liposomes constructed using the components of the invention are stable in serum or blood for several hours. Even under such conditions, the release of active substance is low.

A liposomal vector for the transport of active substances must satisfy at least three preconditions: it must have low toxicity, entrap the active substance firmly and stably, and be compatible with serum or blood.

All of these three preconditions are satisfied by liposomes produced using the substances according to the invention. The liposomes disclosed herein are therefore well suited for therapeutic uses. Other properties supporting such uses are good loadability with active substances and well-directed release of these substances by permeabilization of the membrane at suitable pH values.

Without intending to be limiting, the invention will be explained in more detail with reference to the following examples.

EXAMPLE 1

Synthesis of #59 (histamine-dipalmitoylglycerol succinate)

1.7 g of dipalmitoylglycerol succinate is dissolved in 20 ml of DMF at room temperature. The solution is added with 400 mg of carbonyldiimidazole dissolved in 20 ml of DMF. The mixture is allowed to stir for 1 hour and subsequently added with 300 mg of histamine. The mixture is stirred overnight and concentrated thoroughly in vacuum. The residue is purified using column chromatography on silica gel 60, with chloroform/methanol 10:1 being used as eluant.

EXAMPLE 2

Synthesis of compound #60, 4-(2-aminoethyl)morpholine-di-palmitoylglycerol succinate The synthetic procedure is as in Example 1; instead of histamine, 350 mg of 4-(2-aminoethyl)morpholine is used.

EXAMPLE 3

Preparation of Cationic pH-Sensitive Liposomes 12 mg of a mixture of DMPC/#60/Chol at a molar ratio of 50:15:35 is dissolved in 4 ml of chloroform/methanol (1:1, v/v) and dried completely in a rotary evaporator. The lipid film is hydrated with 4 ml of a corresponding buffer (10 mM KAc, 10 mM HEPES, 150 mM NaCl, pH 7.5) at a lipid concentration of 5 mM using brief ultrasonic treatment (5 minutes). Finally, the suspension is frozen and, following thawing, subjected to multiple extrusions (Avestine Liposo-Fast, polycarbonate filter, pore width 200 nm).

The profile of the zeta potential at various pH values is illustrated in the Table below.

| DMPC/#60/Chol 50:15:35 | |
|---|---|
| pH value | Zeta potential in mV |
| 4 | +54 |
| 5 | +36 |
| 6 | +16 |
| 7.5 | −15 |

EXAMPLE 4

In Situ Preparation of Compound #30 (2-histamine-(1,2-dipalmitoyl-sn-glycero-3-hydroxyphosphoryloxy)ethyl)

Unilamellar liposomes (DPPC/DPPG/cholesterol 40:20:40 mole-%) are suspended at a concentration of 20 mM lipid in a borate buffer (20 mM sodium borate, 120 mM sodium chloride, pH 8.4). 2 ml of this solution is added with 400 µl of a 0.6 M sodium periodate solution, and the mixture is incubated for 30 min in the dark. 1 ml of this suspension is chromatographed on Sephadex G25 in the borate buffer used above. The eluate of the liposome suspension is filled up to make 4 ml.

The liposomes thus oxidized are added with histamine at a final concentration of 20 mM and incubated for 2 hours. Finally, this is reduced with 20 mM sodium borohydride at 4° C. overnight. Excess histamine can be removed by chromatography on Sephadex G25 as above.

EXAMPLE 5

Determination of $pK_a$ Values 15 mg of the respective lipid is dissolved in chloroform and concentrated to dryness in a rotary evaporator until a lipid film is formed. This is taken up in 20 ml of a solution of 0.5% TRITON-X 100 in water and adjusted to pH 3.0 using HCl. The solution is titrated with 20 mM NaOH in steps of 100 µl, and the pH values are recorded.

| Compound | $pK_a$ |
|---|---|
| #60 | 7.2 |
| #59 | 5.5 |
| #30 | 6.7 |

EXAMPLE 6

Preparation of Liposomes Loaded with DNA Plasmids 1.43 mM of the amphoteric lipid is dissolved in chloroform together with the other lipids, depending on the lipid composition of the lipid film. Following removal of the solvent, the lipid film is dried under vacuum overnight. The lipid film is hydrated directly with 1 ml DNA-containing (100 µg DNA/ml) NaAc buffer (10 mM NaAc, 150 mM NaCl, pH 4; slight ultrasonication, followed by rotation above the phase transition temperature for 30 min). This is followed by a freeze/thaw step.

The mixture is extruded 15 times through 400 nm membranes at a temperature 10° C. above the phase transition temperature.

Non-entrapped DNA can be removed by flotation in a sucrose gradient (at pH 7.5; 0.8 M sucrose, 0.5 M sucrose, buffer). The DNA content is determined using the intercalation dye propidium iodide, an increase in fluorescence intensity occurring in case of intercalation into the DNA. To this end, 20 µl of propidium iodide and 6 µl of Triton X-100 (10% in water) are filled up with sample to make 300 µl and measured using a fluorescent plate reader.

EXAMPLE 7

Measurement of the Serum Aggregation of Liposomes

140 µl of human serum is added with 10 µl of a 25 mM liposome suspension using a pipette and mixed thoroughly. 65 µl of this mixture is removed and diluted with 1.5 ml of buffer (HEPES 10 mM, NaCl 150 mM, pH 7.5). The remainder is incubated for 2 h at 37° C., followed by removal of another 65 µl and dilution with 1.5 ml of buffer. The particle size is determined in both samples, using a Malvern Zetasizer 3000. In parallel, control samples likewise incubated for 2 hours at 37° C. are recorded in blank buffer. Non-varied particle size indicates good serum compatibility.

The invention claimed is:

1. A lipid of formula (I):

Cation-spacer2-Y-spacer1-amphiphilic component    (I)

wherein
   (a) the cation is a morpholine group,
   (b) spacer 1 and spacer 2 are each, independently of one another, a linear $C_1$ to $C_8$ alkyl having 0 to 4 hydroxyl groups,
   (c) Y is absent or —(C=O)—O—; —(C=O)—NH—; —NH—(C=O)—O—; —O—; —NH—; —CH=N—; —O—(O=C)—; —S—; —(O=C)—; —NH—(O=C)—; —O—(O=C)—NH—, —N=CH— or —S—S—,
   (d) the amphiphilic component is a compound according to formula (II):

wherein
   $R_1$ and $R_2$ independently are $C_8$-$C_{30}$ alkyl or acyl chains having 0, 1 or 2 ethylenically unsaturated bonds, and
   X is absent or —O—(C=O); —NH—(C=O)—; —S—(C=O)—; —O—; —NH—; —S—; —(O=C)—O—; —S—(O=C)—; —NH—(O=C)—; —N=CH— or —S—S—.

2. The lipid according to claim 1, wherein $R_1$ and $R_2$ are, independently from each other, lauroyl, myristoyl, palmitoyl, stearoyl, oleoyl, or linoleoyl or a corresponding alkyl moiety thereof.

3. The lipid according to claim 1, which has a pKa value between 4 and 6.5.

4. The lipid according to claim 1, wherein X and Y are, independently, —(C=O)—O—, —O—, —NH—, —S—, —O—(O=C), —NH—(O=C)—, or —N=CH—.

5. A liposome which comprises a lipid according to claim 1 and an additional lipid compound.

6. The liposome according to claim 5, which comprises between 5 and 50 mole-% of said lipid of formula I.

7. The liposome according claim 5, wherein the additional lipid compound is phosphatidyl choline, phosphatidyl ethanolamine, ceramide, sphingolipid, tetraether lipid, cholesterol or diacylglycerol, phosphatidyl serine, phosphatidic acid or CHEMS.

8. The liposome according claim 5, wherein the additional lipid compound is an anionic lipid.

9. The liposome according to claim 5, wherein said liposome has an average size of between 50 and 1000 nm.

10. The liposome according to claim 5, which comprises an active substance which is a protein, a peptide, a carbohydrate, a DNA, an RNA, an antisense nucleotide, and/or a decoy nucleotide.

11. The liposome according to claim 8, which further comprises an active substance which is a protein, a peptide, a DNA, an RNA, an antisense nucleotide, or a decoy nucleotide.

12. The liposome according to claim 10, wherein at least 50 μg of active substance per mg lipid is entrapped inside the liposome.

13. Nanocapsules comprising the lipids according to claim 1 and/or a liposomes containing them.

14. A composition which comprises at least one lipid according to claim 1 and a medically active substance which is a protein, a peptide, a carbohydrate, a DNA, an RNA, an antisense nucleotide, and/or a decoy nucleotide.

15. The composition according to claim 14, wherein the active substance is a protein, a peptide, or a DNA.

16. A pharmaceutical composition comprising at least one lipid according to claim 1 and a pharmaceutically tolerable carrier.

17. A kit comprising at least one lipid according to claim 1 and information for providing a formulation comprising said lipid, optionally together with an algorithm of administering said formulation to a recipient.

18. An in vivo transfection system, characterized in that said system includes the liposomes according to claim 5 loaded with genetic material.

19. A method of loading the liposomes according to claim 5 with active substance, characterized in that a defined pH value for encapsulation and a second pH value for removal of unbound active substance is used.

20. The lipid according to claim 1, wherein the acyl is from a fatty acid.